(12) United States Patent
Miller, III

(10) Patent No.: US 7,033,377 B2
(45) Date of Patent: Apr. 25, 2006

(54) SURGICAL DEVICE FOR CAPTURING, POSITIONING AND ALIGNING PORTIONS OF A SEVERED HUMAN STERNUM

(75) Inventor: Archibald S. Miller, III, Tulsa, OK (US)

(73) Assignee: Mavrek Medical, L.L.C., Tulsa, OK (US)

( * ) Notice: Subject to any disclaimer, the term of this patent is extended or adjusted under 35 U.S.C. 154(b) by 168 days.

(21) Appl. No.: 10/857,779

(22) Filed: May 27, 2004

(65) Prior Publication Data

US 2005/0267475 A1 Dec. 1, 2005

(51) Int. Cl.
*A61B 17/08* (2006.01)
(52) U.S. Cl. ............................. 606/213; 606/71; 606/72
(58) Field of Classification Search ................. 606/213, 606/215–218, 60, 69, 70–72, 74
See application file for complete search history.

(56) References Cited

U.S. PATENT DOCUMENTS

| | | | |
|---|---|---|---|
| 4,201,215 A | | 5/1980 | Crossett et al. |
| 5,941,881 A | * | 8/1999 | Barnes ........................ 606/71 |
| 6,007,538 A | | 12/1999 | Levin |
| 6,051,007 A | | 4/2000 | Hogendijk et al. |
| 6,217,580 B1 | | 4/2001 | Levin |
| 6,540,769 B1 | | 4/2003 | Miller, III |
| 6,712,821 B1 | * | 3/2004 | Gabbay ...................... 606/213 |
| 6,872,210 B1 | * | 3/2005 | Hearn ......................... 606/69 |
| 2003/0083694 A1 | * | 5/2003 | Miller, III ................... 606/216 |

OTHER PUBLICATIONS

ALPHA Research; Hemostatic Sternal Closure System; http://www.alpha-research.com/product_4_cc_hsc.html; Alpha Research.
PECTOFIX; PectoFix Surgical Technique Page; http://www.pectofix.com/technique.shtm; PectoFix.

* cited by examiner

*Primary Examiner*—Eduardo C. Robert
*Assistant Examiner*—Jessica R. Baxter
(74) *Attorney, Agent, or Firm*—Crowe & Dunlevy, P.C.

(57) ABSTRACT

A surgical device for capturing, positioning and aligning portions of a severed human sternum via positioning around the costal cartilage portion of each of a paired set of ribs located on opposite sides of the severed sternum while simultaneously contacting and substantially surrounding the anterior and posterior portions of the sternum comprising impermanently joined insertion and insertion guide attachment members, each of the members having first and second end portions, first and second side portions, a body portion, anterior and posterior surfaces, two crescent formed leg portions with angularly displaced foot portions, a plurality of sternum, rib and costal cartilage engagement surfaces and, a rotary lock member pivotally attached to the insertion guide member, and further comprising a capturing mechanism having angularly displaced teeth-like structures on a first side cooperating with reciprocating teeth like structures integrated on a first side of the insertion member to position, secure in place and operatively combine the insertion member, rotary lock and insertion guide members.

12 Claims, 9 Drawing Sheets

SURGICAL DEVICE FOR CAPTURING, POSITIONING AND ALIGNING PORTIONS OF A SEVERED HUMAN STERNUM

REFERENCE TO PENDING APPLICATIONS

This application is not related to any pending application.

REFERENCE TO MICROFICHE APPENDIX

This application is not referenced in any microfiche appendix.

FIELD OF INVENTION

The present invention relates in general to surgical positioning devices and more particularly to a surgical device for capturing, positioning and aligning portions of a severed human sternum.

BACKGROUND OF INVENTION

Wire closures are widely represented in the contemporary art as a recognized means for closing the sternum following a mid-line sternotomy. Examples of such contemporary closure systems are marketed under a variety of device/methodology names including but not limited to the Hemostatic Sternal Closure® system which proclaims to be a major innovation based upon proven principals and cardiovascular surgery. At the time of this writing further documentation with respect to the Hemostatic Sternal Closure System may be found at the website http://www.alpha-research.com.products_4_cc_hsc.html. Another example of a wire dependent closure system is marketed under Pectofix Surgical Technique Information with respect to deployment of this technique and its associated device can be found at the website http://www.pectofix.com/technique.shtm.Other wire closure systems are known to those skilled in the art, have been used in the past, and indeed continue to be used with less than desirable results.

Widely recognized deficiencies with respect to wire based closure devices include an implementation/deployment time typically averaging 15–20 minutes per mechanism. Such an excessive time requirement translates, of course, into increased operating room costs, increased doctor, staff and insurance costs, and increased doctor fatigue. Perhaps of greater significance however are the numerous stresses caused and long associated with deployment of wire based sternum closure devices including patient pain, patient infection, pneumonia, tissue tears, wire disengagement and loosening, chest openings, and post-op emergent returns. All the afore-noted conditions result from inexact and undue stress conditions associated with wire closure devices in turn, and consistently result in slower patient discharges and unnecessary costs for the patient and community. In stark contrast, the instant invention requires an implementation time that is reduced by more than 90% from that of wire devices requiring only one to two minutes implementation time per clamp, virtually eliminates multi-lateral stresses through physics and strength, and totally eliminates the necessity for bone punctures required of wire suture based devices.

A variety of sternal disruptive forces exasperate the very intention of wire based systems. Forces associated with sternonomies include but are not limited to the rectus abdominus muscle exerting an uneven pull, a lateral pull by pectoralis muscles, forces generated by valsalva action and anterior/posterior displacement of hemi-sternum via respiratory muscle action. With respect to contemporary art wire based systems, such disruptive forces typically result in one or more of the following conditions: (a) wires cutting into bones; (b) sternal fragmentation; (c) broken wires; and (d) off-side sternotomy.

In view of the deficiencies of wire based clamping surgical devices, and further in view of the life threatening conditions associated with failure of such devices, newer technology has been recognized as superior to the wire devices. Stated succinctly, such devices are generically referred to as clamp closures. Though other clamp closure devices have been presented as effectuating an improvement over wire devices, no contemporary clamp closure provides the novel aspects and benefits afforded by the instant device for capturing, positioning and aligning portions of a severed human sternum via the device's unique structure for capturing and positioning the costal cartilage (notch) portion of each of a paired set of ribs located on opposite sides of a severed sternum while simultaneously contacting and substantially surrounding the anterior and posterior portions of the sternum and thereby preventing severed sternal halves from moving relative to one another and precluding rostral and vertical bone shearing travel. Consequently, the unique structure of the instant invention addresses and resolves many of the problems associated with contemporary wire systems, and indeed, contemporary clamp closures.

U.S. Pat. No. 6,051,007 issued Apr. 18, 2002 to Mike Hogendijk and Troy Chapman, subsequently assigned to Coravascular Incorporated and filed May 2, 1998 purports to disclose and claim a sternal closure device comprising first and second clamps. The first and second clamps have a generally tubular portion and the second clamp has a portion that is slidably receivable in the tubular portion, and a lock configured to retain said second clamp within said first clamp. A surgical instrument for laterally moving opposed sternal clamps toward one another is also disclosed. The instrument comprises first and second grasping members generally linearly slidably coupled to one another.

As clearly distinguished from the instant invention the benefits, teachings and claims of the '007 patent lack the multiplicity of sternum engagement services and more importantly the "surrounding" capability of the instant invention with respect to anterior and posterior sternal halves as well as opposing rib members of a rib pair located on either side of the severed sternum. Such distinguishing characteristics allow for superior assistance with respect to normal pulmonary mechanics; enhance positioning and accelerate recuperation time associated with procedures requiring the severing of human sternum.

U.S. Pat. No. 6,217,580 B1 purports to disclose and claim a method of closing a patient's sternum following a sternotomy as indicated with respect to U.S. Pat. No. 6,051,007 above the '580 patent, though issuing a year subsequent to that of Hogendijk ('007 patent) continues to lack the resilience positioning and capturing benefits and claims of the instant invention. Though the '580 patent is limited to a method relating to the closing of a patient's sternum it is to be noted that the '580 patent relies upon bringing opposed legs of clamp members into overlapping relationship to one another in sharp distinction to the instant invention. Such overlapping relationship and reliance upon countersunk regions of a clamp member to present a substantially flush upper surface does not provide for the securing strength offered by the insertable relationship of the instant invention with respect to insertion guide and insertion guide members. Further and perhaps of greater importance, like the '007 patent, the '580 patent continues to present deficiency with respect to preventing rostral and vertical sheering of severed sternum halves in that it fails to capture or combine the positioning/securing benefits of aligning severed sternal halves in combination respective rib pair members.

U.S. Pat. No. 4,201,215 issued May 6, 1980 to E. S. Crossett L. L. purports to disclose and claim an apparatus and method for closing a severed sternum. The device of Crossett, as disclosed, is dimensionally deficient with respect to the rib capturing and positional expectancies of the instant invention. More specifically, the devise of Crossett is intended to be deployed between subsequent sets of rib pairs as opposed to capturing (surrounding) rib pairs attached to either half of a severed sternum. Further, the devise of Crossett does not provide the pulmonary assistance offered by the instant invention in that it would appear the body portion of the Crossett devise relies upon structural displacement across the posterior portion of the sternum. Such positioning and structural dynamics render the Crossett device incapable of presenting the angularity offset required to evenly match and align the anterior portions of the severed sternum without inducing undue stress.

In addition to enhancing the art beyond that of contemporary art sternum closure devices, the instant invention provides benefit to the following: patients, doctors, hospitals and insurance. For patents, the rapid and effective implementation of the present invention results in lower patient pain, infection, bleeding, requires fewer blood transfusions, fewer post-op emergent returns and greater satisfaction. For doctors benefits include but are not limited to ease of application, less fatigue, better efficacy rate, less time in the operating room and more time with patients or their families. For hospitals, the efficiency of the present invention results in lower numbers of corrective procedures, lower operating room costs (less time), lower doctor/staff costs. With respect to insurance coverage benefits, the present invention facilitates lower up front costs as it deployment induces less infections, less bleeding and less time under anesthesia. All resulting in lower risk to the patients, lower back end costs with lower post-op emergent returns, and indeed, lower overall hospital costs.

SUMMARY OF INVENTION

A surgical device for capturing, positioning and aligning portions of a severed human sternum via the device's positioning around the costal cartilage portion of each of a paired set of ribs located on opposite sides of the severed sternum while simultaneously contacting and substantially surrounding the anterior and posterior portions of the sternum thereby precluding rostral and vertical bone shearing travel by preventing severed sternal halves from moving relative to one another. In so doing the device of the instant invention discloses and claims impermanently joined insertion and insertion guide attachment members with each of said members having first and second end portions, first and second side portions, a body portion, anterior and posterior surfaces, two crescent formed leg portions with angularly displaced foot portions, a plurality of sternum, rib and costal cartilage engagement surfaces. A rotary lock member is pivotally attached to the insertion guide member, and further comprises a capturing mechanism having angularly displaced teeth-like structures on a single side which cooperate with reciprocating teeth like structures integrated on a single side of the insertion member to position, secure in place and operatively combine the insertion member, the rotary lock and the guide member.

BRIEF DESCRIPTION OF DRAWINGS

For a more complete understanding of the present invention, and the advantages thereof, reference is now made to the following descriptions taken in conjunction with the accompanying drawings, in which.

DETAILED DESCRIPTION OF THE INVENTION

While making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

The claims and specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

Figure 1:
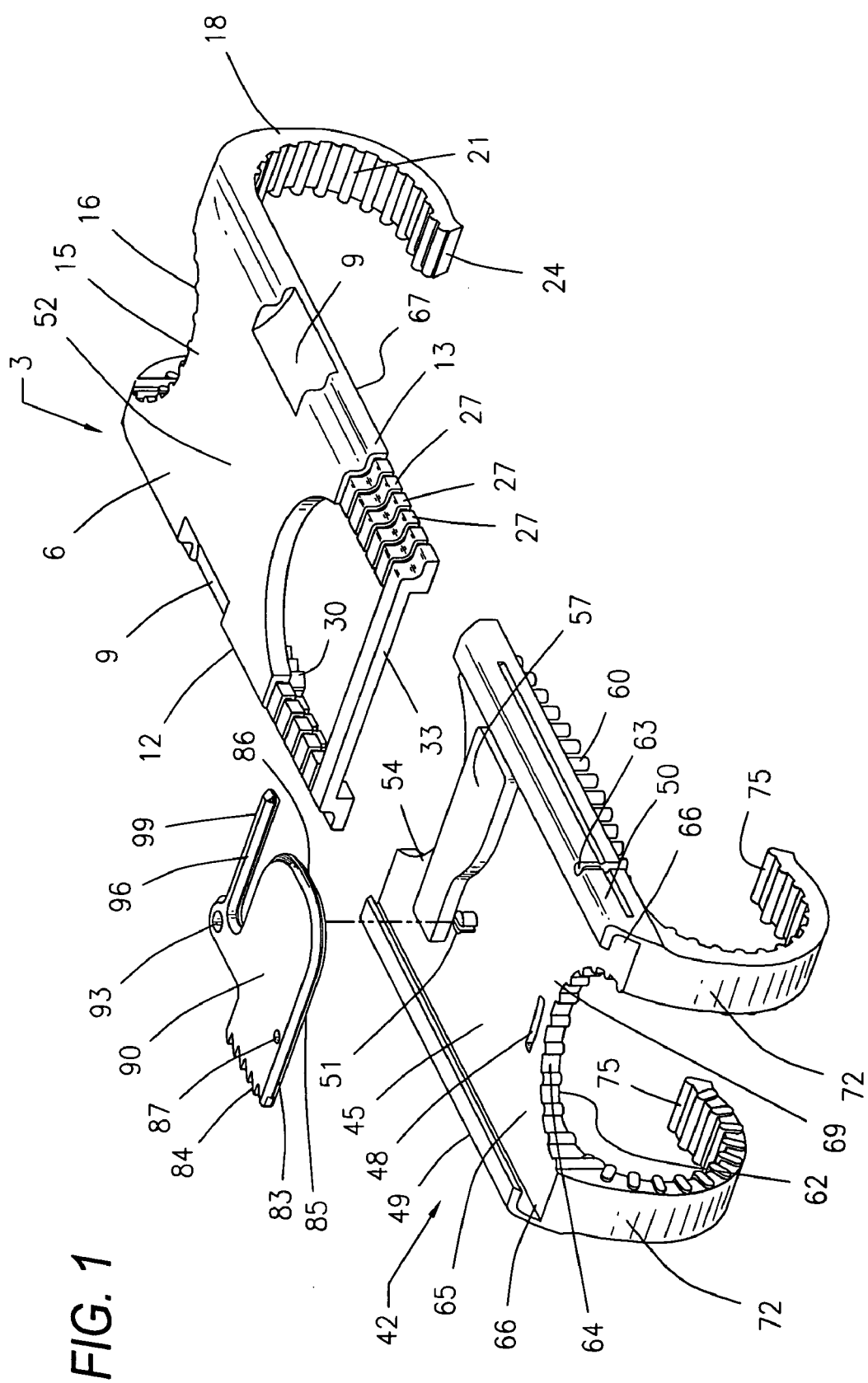
FIG. 1 is an exploded view representative illustration of the embodiment of FIG. 1 providing detail with respect to internalized elements of the invention.

Referring now to the drawings wherein depicted elements are not necessarily shown to scale and wherein like or similar elements are designated by the same reference numeral through the several views. FIG. 1 discloses an exploded view representative illustration of the embodiment providing detail with respect to internalized elements of the invention. Turning now to FIG. 1.

In FIG. 1 it may be observed where an embodiment of the instant invention is comprised of impermanently joined insertion and insertion guide attachment members (3, 42) with each of said members having respective first (33, 69) and second (54, 15) end portions, first (12, 49) and second (13, 50) side portions, body portions (6, 45) having anterior (52, 65) and posterior (62, 67) directed surfaces. Further, each of said attachment members (3,42) comprise two crescent formed leg portions (18, 72) with angularly displaced foot portions (24, 75) and a plurality of sternum, rib and costal cartilage engagement surfaces. The sternum engagement surfaces of the instant invention include but are not necessarily limited to, non-attached end portions of each of a plurality of variable length cylindrical pegs 60, located on opposing side portions (49, 50) of the insertion guide 42 members posterior surface 62. When deployed said variable length cylindrical pegs 60 contact the anterior surface of each portion of severed sternum. Costal cartilage contact portions are designated as element 62 for insertion guide member 42, and as element 16 for insertion member 3. It is to be noted that the costal cartilage contact surfaces (62, 16) disclose an irregularly contoured surface to provide for enhanced gripping/positioning once the invention is deployed or "knuckled" against the costal cartilage.

Continuing with FIG. 1, it is further disclosed where rotary lock member 90 is pivotally attached to insertion guide member 42 via pivoting pin 51 insertion through pivoting guide aperture 93. The rotary lock 90 may additionally comprise a sharpened, beveled edge 83 located along the periphery of the lock's first end 85 and second side portion 86 to assist in cutting through or otherwise displacing infringing tissue growth.

The lock 90 of the instant invention provides for a unique capturing mechanism having angularly displaced teeth-like structures 84 which cooperate with reciprocating teeth-like structures 30 positioned along the posteriorly directed surface of insertion member 3, first side 12 to position, secure in place and operatively combine said insertion member 3, said rotary lock 90, and said insertion guide member 42. Also shown in FIG. 1 with respect to rotary lock member 90 is a rapid release insertion bore 87 and resiliently tensioned rapid disengagement arm 96 having a positioning shoulder 99 which compressively abuts positioning block 57.

The instant invention provides for two emergency rapid release mechanisms to disengage the sternum clamp. The first of said emergency release mechanisms is disclosed via the cooperation of a needle nose plier-like device's insertion within lock's rapid release insertion bore 87 and rapid release positioning divot 63. By compressing this plier-like apparatus once so deployed, lock 90 rotates and compresses its resiliently tensioned spring member 96 positionally abutting positioning block 57. Lock 90 axially rotates upon pivoting pin 51 which insertably traverses pivoting pin aperture 93 and precipitates the release of the lock's teeth-like capturing mechanism 84 from reciprocal teeth 30. Detailed discussion and illustration relating to the first of the invention's two emergency release structures and practices will be discussed in association with FIGS. 4 and 5.

Figure 12:
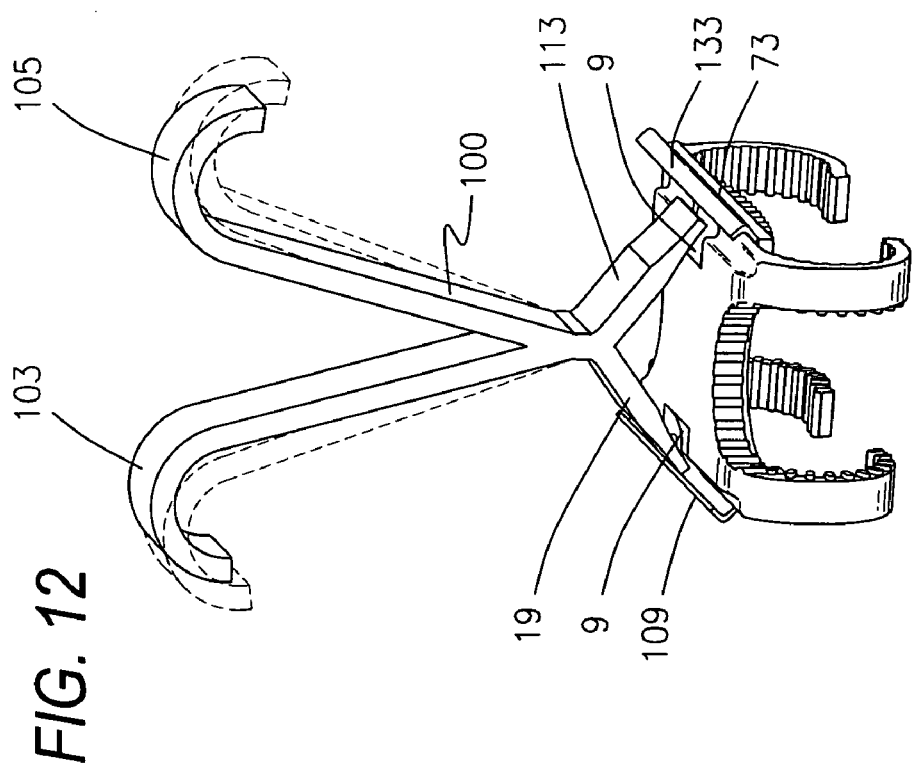
FIGS. 11 and 12 respectively illustrate the positioning and deployment of the instant invention's emergency release tool (ERT).

A second emergency release mechanism allows for deployment via a complementing emergency release tool described in association with FIGS. 12 and 13. The tool is deployed against biasing guides 9 located generally along first 12 and second 13 sides of insertion member 3. Detailed discussion and practices of complementing emergency release tool and association deployment methodology shall be discussed in association with FIGS. 11 and 12. For purposes of continuing discussion with respect to FIG. 1, insertion member 3 as illustrated in FIG. 1 further comprises a plurality of biasing guides 9 located on opposite sides of said insertion member 3 which allows leveraging insertion therein of a complementary prying tool to forcibly disengage insertion 3 and insertion guide members 42 and thus facilitate rapid/emergency removal of the invention, once positionally deployed.

Figure 2:
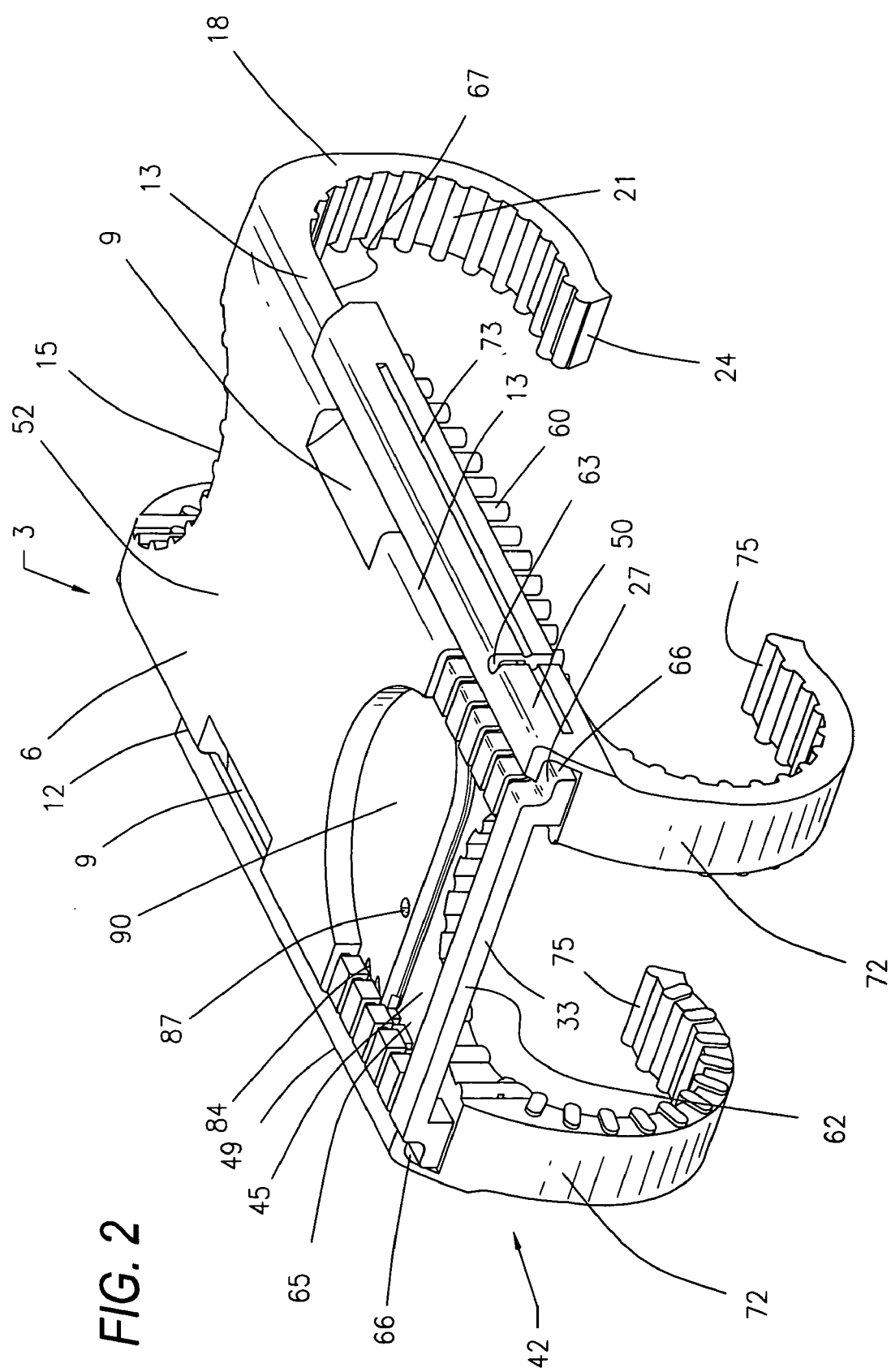
FIG. 2 is a view of a representative embodiment of the instant invention illustrating body and body insert portions in a joined or "closure" mode.

Additionally shown in FIG. 1 are severable insertion guide contact sections 27 which may be individually or collectively removed from the insertion member to allow for customized patient sizing of the clamp once deployed. A further benefit and intended object such dynamically customized severing of contact members 27 serves to preemptively extraneous contact sections 27 from areas likely to present opportunity for invasive tissue growth. Turning now to FIG. 2.

FIG. 2 illustrates a representative view of an embodiment of the instant invention illustrating body and body insert portions in a joined or closed mode.

Figure 3:
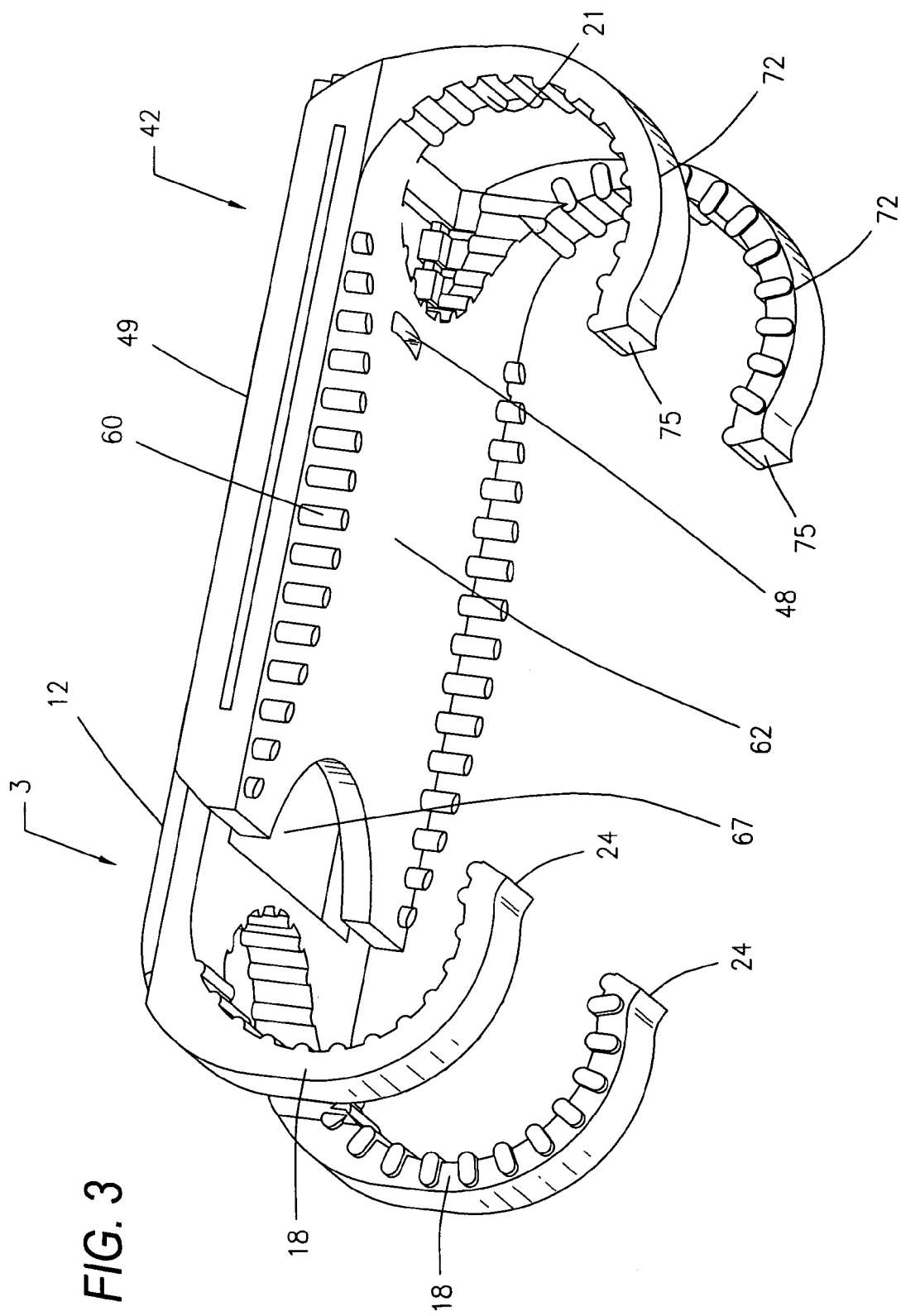
FIG. 3 is a representative illustration of the instant invention providing a view of the invention from a posterior perspective.
Figure 11:
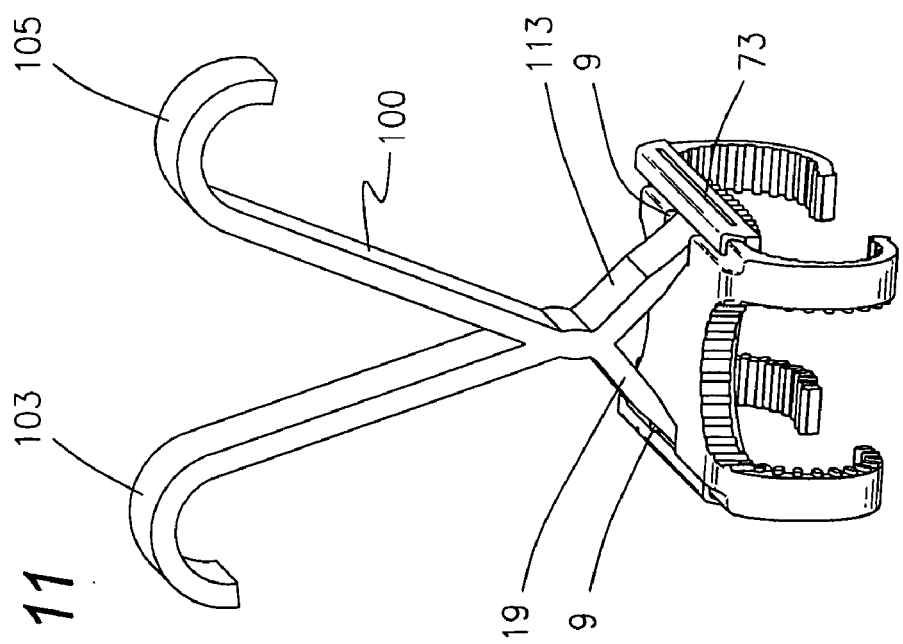

In FIG. 2 it is disclosed where insertion member 3 has been insertably accommodated within guide member section 42. Most particularly, attention is drawn to the receiving guide channel 66 designated for this purpose and into which severable insertion guide contact sections 27 and insertion lip portions located on first 12 and second sides 13 of insertion member 3 have been positioned in the invention's closure mode. It will be further appreciated in FIG. 2 where insertion bore 87 is observed positionally overlying emergency release channel 48 (shown in FIG. 1) not illustrated FIG. 2. As earlier discussed in association with FIG. 1, the deployment of the emergency release of the rapid sternum closure (RSC) device of the instant invention can be effectuated utilizing a compressing plier-like apparatus with pointed/needle nose surfaces to cooperatively engage channel 48, bore 87 and divot 63 to facilitate the compression of tension arm 96 and rotation of lock 90. In addition to elements previously discussed in association with FIGS. 1 and 2 it is to be noted where element 73 discloses to a stress relief channel 73 located on the outermost surfaces of the invention's receiving guide channels 66. The stress relief channel 73 is incorporated within the outermost portion of both channels of the instant invention and as will be discussed in association with FIGS. 11 and 12 provides a means for rapid disassociation of the instant invention from a severed sternum when utilized in conjunction with biasing guide 9 to pry or otherwise disassociate attachment guide member 42 from insertion member 3. Turning now to FIG. 3.

FIG. 3 is a representative illustration of the instant invention providing posterior perspective view of the invention.

In FIG. 3 the variable length cylindrical pegs 60 of the instant invention may be clearly observed. Though in the illustrated embodiment of the instant invention it is shown where cylindrical structures are of variable, though fixed lengths, it is easily envisioned where compressible "pins" would serve the function to custom fit the posterior directed surface 62 of the clamp 42 to the anterior-most surface of each part of a severed human sternum. The column-like pins 60 as illustrated in FIG. 3 typically form fit against the manubrium portion of the severed sternum with respect to the invention's uppermost rib pair deployment and the body section of a severed sternum with respect to the invention's lower portion rib pair deployment.

Figure 4:
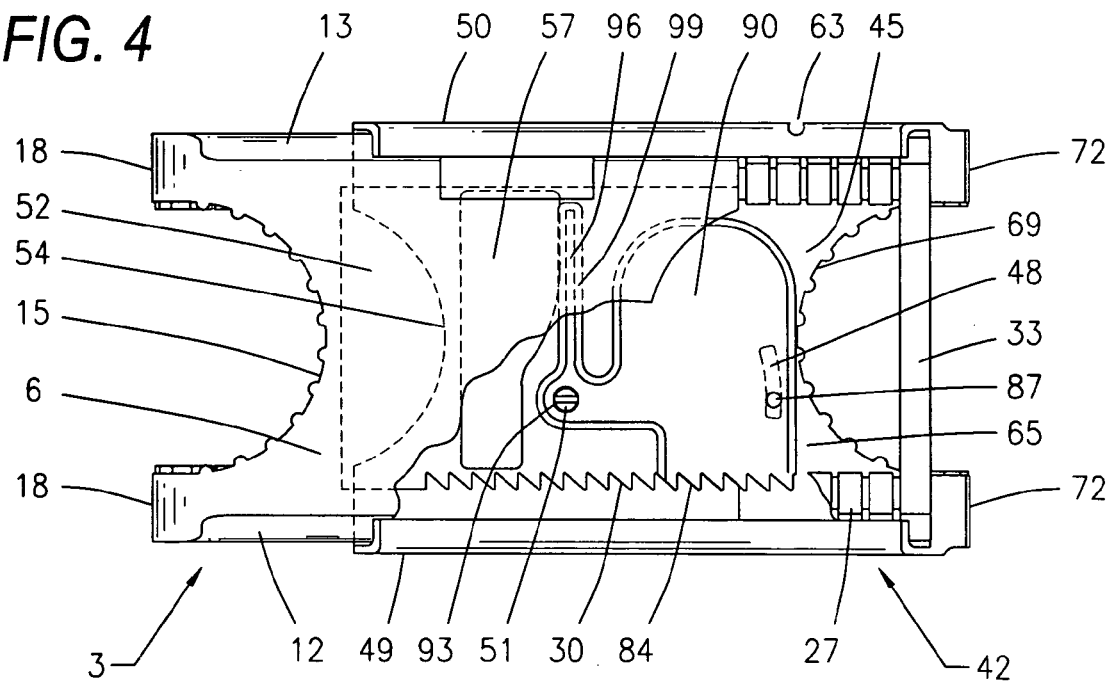
FIG. 4 is a plan view illustration of the instant invention providing further detail with respect to the inventions rotary lock member in an engaged and secured position.
Figure 5:
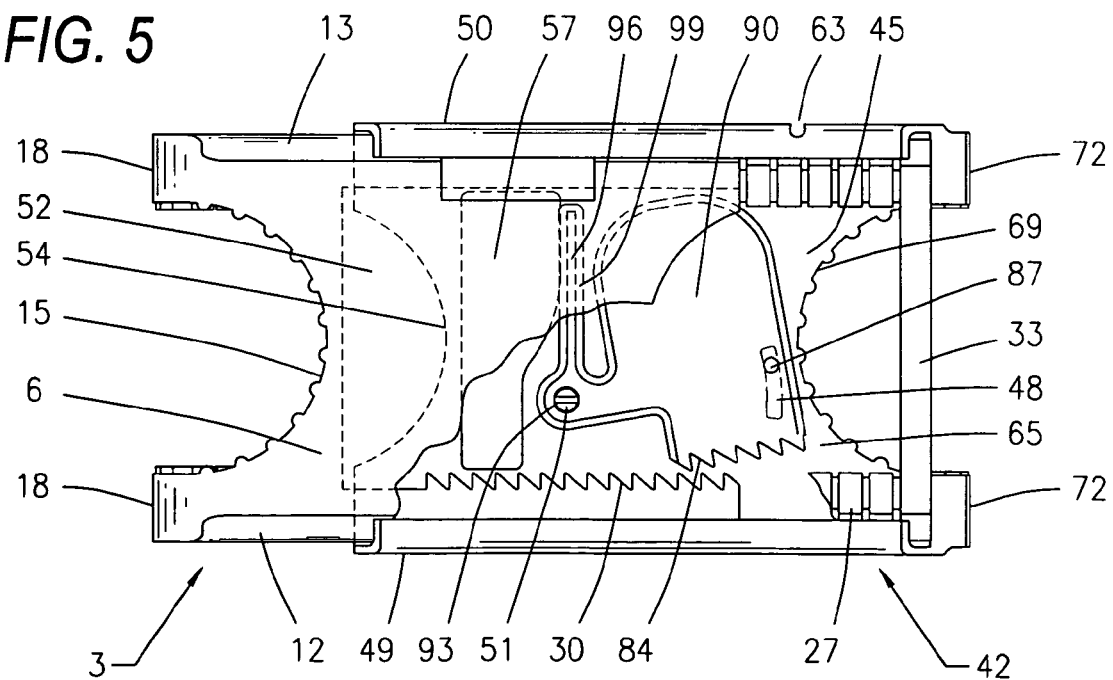
FIG. 5 is a plan view illustration of the instant invention providing further detail with respect to the inventions rotary lock member in a disengaged and position.

Also shown in FIG. 3 in greater detail are foot portions 75 and 24 wherein such portions allow for the surrounding capture of severed sternum surfaces and operate in compressible communication with variable length cylindrical pins 60 to effectuate an angular displacement of a severed sternum, replicating the sternum's normal anatomical configuration to cooperatively enlist normal pulmonary mechanics to assist in the healing process. Also shown in FIG. 3 are the crescent-shaped legs 18, 72 of the instant invention which substantially surround opposing ribs of a rib pair. The legs (18,72) typically, though not limitedly, embody irregularly shaped surfaces (19, 21) and are engineered to provide enhanced gripping contact with rib sections and facilitate positioning of the device. Turning now to FIGS. 4 and 5.

FIGS. 4 and 5 disclose a plan view illustration of the instant invention providing further detail with respect to the inventions rotary lock member in an engaged and disengaged mode.

Figure 6:
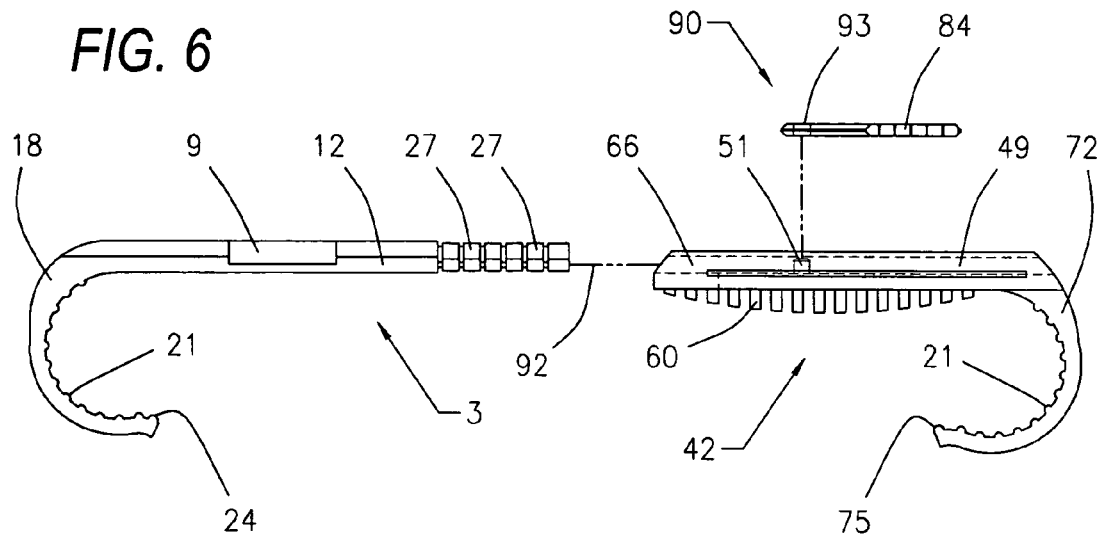
FIG. 6 is a representative illustration of the instant invention providing greater detail of the inventions rotary lock positioning and variable length cylindrical pegs as viewed from a patients head viewing downwardly.

Referring to FIGS. 4 and particularly 5 it is disclosed where deployment of the invention's first emergency release mechanism has been effectuated. In so doing, lock 90 pivots upon pin 51 which disengages teeth-like structures 84 of lock 90 from complementing teeth-like structures 30 of insertion member 3. Further discussion with respect to the manner in which rotation of lock member 90 may be effectuated is consistent with that as discussed in association with FIGS. 1 through 3. Turning now to FIG. 6.

FIG. 6 is a representative illustration of the instant invention providing greater detail of the inventions rotary lock positioning and variable length cylindrical pegs as viewed from a patients head viewing downwardly.

Figure 7:
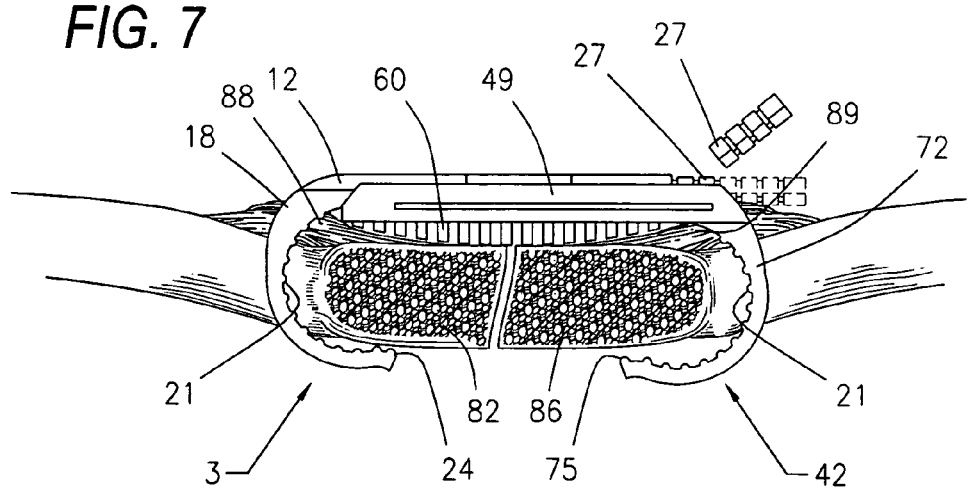
FIG. 7 is a representative illustration of the instant invention shown as deployed substantially surrounding a rib pair, capturing the costal cartilage and providing further detail with respect to the invention's break away customizing fit capability.

In FIG. 6 it is disclosed where insertion member 3 is to be received my insertion guide member 42 with insertion member 3 proceeding along line 92. Cylindrical or similarly intended peg-like structure 60 when viewed from the perspective in FIG. 6 provide a convex shaped dimensioning allowing the generally centermost pegs to align with the concave portion of the manubrium with respect to the instant invention's upper rib pair deployment and concave shaped portion of the manubrium in the invention's deployment with respect to lower rib pair/sternum deployment. FIG. 6 illustrates in phantom the receiving channel 66 within insertion guide member 42 for receiving insertably positioned severable insertion guide contact member 27 and (from this illustration's perspective) first side member 12 of insertion member 3. FIG. 6 further provides additional disclosure with respect to crescent shaped leg portions 18 and 72 and foot portions (24, 75). Attention in FIG. 6 is drawn to irregularly shaped surfaces 21 which typically though not limitedly are integrated within the concave portion of the crescent leg member to facilitate enhanced contact service and grasping of severed sternal halves during deployment of the invention. Consequently from the view provided in illustration 6 it is clear the instant invention provides sternum contact services via pin-like structure 60, feet portions (24, 75), irregular surfaced contact portions 21 which maintain contact with each half of a severed sternum along the invention's concave dimensioning and further maintains contact with either side of each rib attached to severed sternum and to which said invention has been dimensioned and positioned to surroundingly capture the rotary lock pivoting pin 51 is illustrated aligned for positioning insertion through pivoting guide aperture 93 of rotary lock 90. Further shown in FIG. 6 are said rotary lock's 90 angularly displaced teeth-like structures 84 which cooperate for securing purposes with reciprocating teeth-like structures 30 integrated and positioned along the posterior directed surface of first side 12 of insertion member 3. Turning now to FIG. 7.

FIG. 7 is a representative illustration of the instant invention providing greater detail of the inventions rotary lock positioning and variable length cylindrical pegs as viewed from a patients head viewing downwardly.

Figure 8:
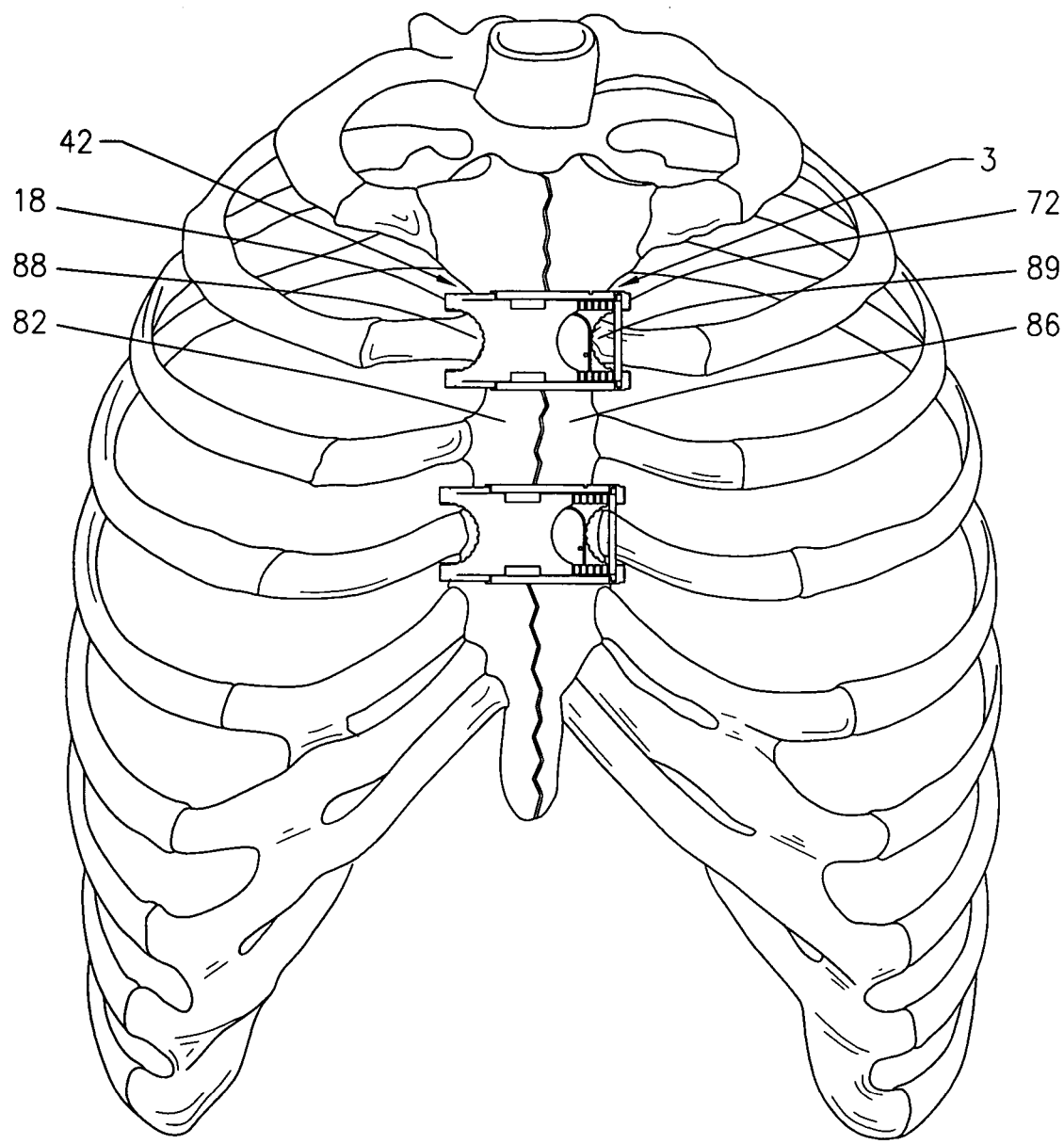
FIG. 8 is a representative anterior view illustration of the instant invention as deployed and substantially surrounding two rib pairs to capture position and align portions of a previously severed sternum.
Figure 9:
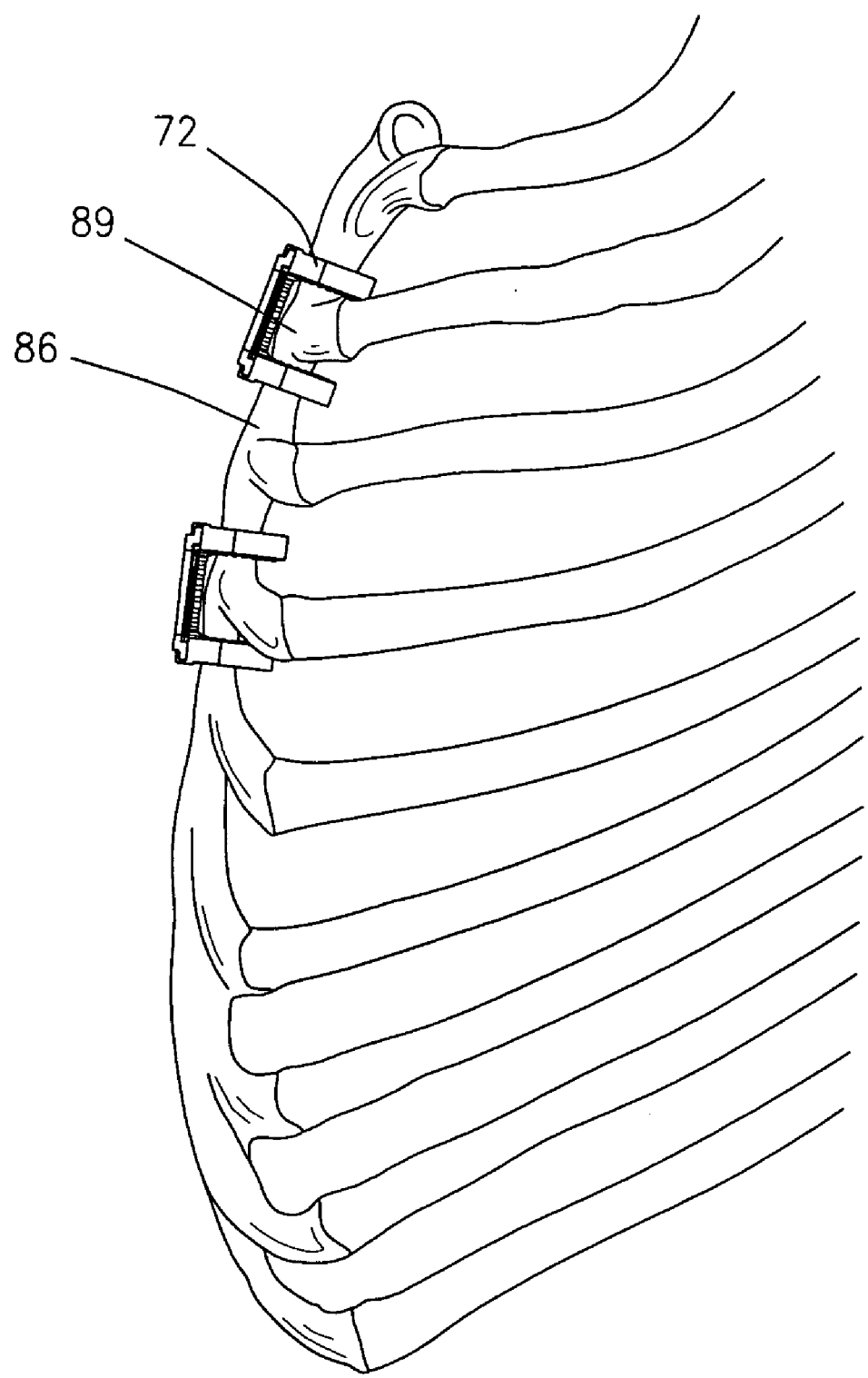
FIG. 9 is a side view illustration of the deployment of the invention illustrated in FIG. 8.
Figure 10:
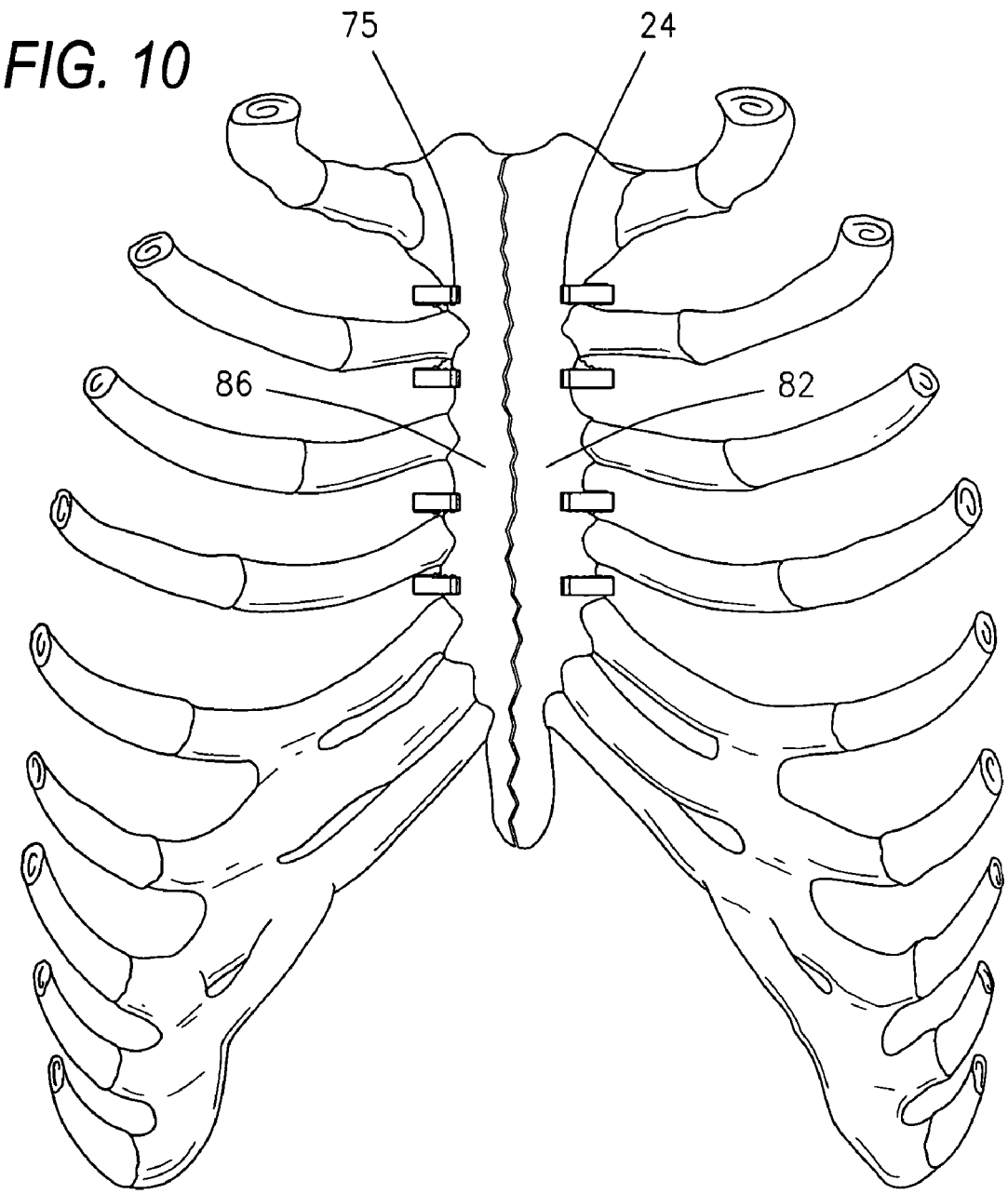
FIG. 10 is a posterior view of the instant invention as deployed and illustrated in FIGS. 8 and 9.

FIG. 7 illustrates in additional detail the pin-like structure 60 of the instant invention maintaining contact with the manubrium portions of a severed sternum (82, 86). It may be seen in FIG. 7 where the instant invention provides for complete surrounding and positioning of the manubrium/ sternum by maintaining contact portions as noted in association with FIG. 6. Said contact portions typically including but not being limited to foot portions (24, 75), leg member sections irregular surface 21 column-like structure 60 and costal cartilage sections (88, 89) wherein said cartilage effectively capture the horizontally displaced portions of clamp member (42, 3). FIGS. 8, 9 and 10 providing further detail with respect to the enhanced positioning and capturing capabilities of the instant invention. Turning now to FIGS. 8 through 10.

In FIGS. 8 through 10 it can be seen where a severed sternum halves are denoted as elements 82 and 86. The clamp of the instant invention 3 extends across both halves of the severed sternum 82 and 86 via crescent shaped leg portions 72 and 18 effectively capture and surround the costal cartilage portions of each rib of a rib pair attached to said severed sternum. It is noted where portions 86 and 89 of the costal cartilage effectively capture said clamp 3 and provide a "knuckling" or otherwise form fitting structure to further assist the inventions secure deployment and positioning.

FIG. 10 provides a posterior view of severed sternum 82 and 86 and allows for observation of foot portions 24 and 75 maintaining contact with said posterior sternum portions to effectively capture and position the sternum consistent with positioning necessary to effectuate normal pulmonary mechanics. Turning now to FIGS. 11 and 12.

FIGS. 11 and 12 disclose and respectively illustrate the positioning and deployment of the instant invention's emergency release tool (ERT).

FIG. 11 illustrates the emergency/complementary release tool 100 leveraging arms 103 and 105 are axially attached to prying portions 19, 113 for insertion into biasing guides 9 as discussed in association with FIG. 1 and incorporated within the body structure of insertion member 3.

In FIG. 12 it seen where complimenting tool's 100 leveraging portions 103 and 105 are manipulated in a manner to expand outwardly sections 109 and 133 to create stress along section 73 of insertion guide member to effectuate the peeling back or breaking away of said guide member and thus facilitating emergency release of the clamp of the instant invention.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

The invention claimed is:

1. A method for capturing, positioning and aligning portions of a severed human sternum via the device's deployment around the costal cartilage portion of each of a paired set of ribs located on opposite sides of the severed sternum while simultaneously contacting and substantially surrounding the anterior and posterior portions of the sternum thereby precluding rostral and vertical bone shearing travel by preventing severed sternal halves from moving relative to one another comprising:

providing a sternum closure device comprising impermanently joined insertion and insertion guide attachment members, each of said members having first and second end portions, first and second side portions, a body portion, anterior and posterior surfaces, two crescent formed leg portions with angularly displaced foot portions, and a plurality of sternum, rib and costal cartilage engagement surfaces, the insertion guide member individually comprising a rotary lock positioning block, a plurality of variable length cylindrical pegs located on opposite sides of the insertion member's posterior surface, a rotary lock pivoting pin, a disengagement tool positioning divot, and a pair of guide sections to position and removably receive said insertion member when inserted therein, the insertion member individually comprising a biasing guide to allow leveraging insertion therein of a prying tool to forcibly disengage insertion and insertion guide members from one another, and a plurality of severable insertion guide contact sections which may be individually or collectively removed, and a rotary lock member pivotally attached to said insertion guide member, the locking member further comprising a capturing mechanism having angularly displaced teeth-like structures on a first side which cooperate with reciprocating teeth-like structures integrated on a first side of said insertion member to position, secure in place and operatively combine said insertion member, said rotary lock and said insertion guide member; and, insertably joining said insertion member within said insertion guide member in a manner to capture the costal cartilage portion of each of a paired set of ribs located on opposite sides of a severed human sternum while simultaneously engaging and substantially surrounding the anterior and posterior portions of the sternum.

2. A sternal closure device comprising:
an insertion member having a body portion and a leg portion, wherein the body portion includes teeth-like structures along a first side of the body portion;
an insertion guide member configured to receive the insertion member, wherein the insertion guide member includes a body portion and a leg portion; and a rotary lock rotatably mounted to the body portion of the insertion guide member, wherein the rotary lock includes teeth-like structures that engage or release the teeth-like structures on the insertion member as the rotary lock rotates.

3. The sternal closure device of claim 2, wherein each of the insertion member and insertion guide member include two leg portions.

4. The sternal closure device of claim 3, wherein the leg portions on each of the insertion member and insertion guide member are crescent shaped.

5. The sternal closure device of claim 2, wherein each of the insertion member and insertion guide member include a plurality of sternum, rib and costal cartilage engagement surfaces.

6. The sternal closure device of claim 2, wherein the insertion guide member includes a pivot pin extending from the body portion and the rotary lock further includes a pivot aperture that is configured to accept the insertion guide member pivot pin.

7. The sternal closure device of claim 2, wherein the rotary lock further includes a rapid release insertion bore.

8. The sternal closure device of claim 2, wherein the insertion guide member further includes a positioning block and the rotary lock includes a spring member adjacent to the positioning block that opposes the rotation of the rotary lock.

9. The sternal closure device of claim 2, wherein the rotary lock includes a sharpened beveled edge.

10. The sternal closure device of claim 2 further comprising cylindrical pegs located on the posterior side of the insertion member.

11. The sternal closure device of claim 2, wherein the insertion member further comprises a biasing guide configured to accept a prying tool to forcibly disengage the insertion member and insertion guide member.

12. A method for closing a severed sternum with a sternal closure device, the method comprising:
engaging a first portion of the severed sternum with an insertion member that includes two legs that are configured to straddle a first rib connected to the first portion of the severed sternum;
engaging a second portion of the severed sternum with an insertion guide member that includes two legs that are configured to straddle a second rib connected to the second portion of the severed sternum;
inserting the insertion member into the insertion guide member to approximate the severed sternum; and
securing the severed sternum in an approximated position by locking the insertion member and the insertion guide member in a closed position by engaging teeth-like structures on the insertion member with corresponding teeth-like structures on a rotary lock that is rotatably mounted to the insertion guide member.

* * * * *

UNITED STATES PATENT AND TRADEMARK OFFICE
CERTIFICATE OF CORRECTION

PATENT NO.        : 7,033,377 B2                                      Page 1 of 1
APPLICATION NO.   : 10/857779
DATED             : April 25, 2006
INVENTOR(S)       : Archibald S. Miller, III It is certified that error appears in the above-identified patent and that said Letters Patent is hereby corrected as shown below:

On Title Page Item (56) Col. 2
Other publications replace ".com/products_" with --.com/products.--

Column 4
Line 21 replace "disengaged and position" with --disengage position--

Column 4
Line 25 replace "a patients head" with --a patient's head--

Column 7
Line 30 replace "patients head" with --patient's head--

Column 7
Line 32 replace "received by insertion with --received by insertion--

Column 8
Line 4 replace "patients head" with --patient's head--

Column 8
Line 21 replace "where a severed" with --where severed--

Column 8
Line 47 replace "it seen" with --it is seen--

Signed and Sealed this

First Day of August, 2006

JON W. DUDAS
*Director of the United States Patent and Trademark Office*